US00PP08122P

United States Patent [19]

Jessel, Jr.

[11] Patent Number: Plant 8,122

[45] Date of Patent: Feb. 2, 1993

[54] CARNATION PLANT NAMED CFPC AMETHYST

[75] Inventor: Walter H. Jessel, Jr., Salinas, Calif.

[73] Assignee: California Florida Plant Co., L.P., Salinas, Calif.

[21] Appl. No.: 678,550

[22] Filed: Mar. 28, 1991

[51] Int. Cl.[5] ..... A01H 5/00

[52] U.S. Cl. ..... Plt./70.5

[58] Field of Search ..... Plt./70–72

*Primary Examiner*—Howard J. Locker

*Attorney, Agent, or Firm*—Christie, Parker & Hale

[57] ABSTRACT

A new and unusual carnation of mauve coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is CFPC Amethyst.

Among the novel characteristics possessed by the new variety which distinguishes it from its parents and all other varieties of which I am aware its unusual and distinctive mauve or smoky orchid flower coloration. The new variety exhibits very uniform flowering on a very vigorous and free-breaking plant habit and produces strong straight sprays. Flowers response is on average five months from planting to flowering.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development (tight bud, partially opened bud and full bloom), depicted in color as nearly true as it is reasonably possible to make the same in a color illustration of this character.

DESCRIPTION OF THE NEW VARIETY

The new variety, CFPC Amethyst, produces flowers of unusual color on strong stems. It has excellent flower production and the bud count does not drop during low-light periods. Its attractive and unusual coloring, as well as the other characteristics heretofore and hereinafter described, make it especially suitable for commercial cut flower production in greenhouses as a spray. The new variety is fertile as a female parent and appears to be male sterile.

The following is a detailed description of my new variety, with color terminology in accordance with The Royal Horticultural Society of Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouse at Fremont, Calif. The height of plant and flower and foliage size are established as an average using standard commercial cultural practices.

Name: CFPC Amethyst.

Classification:

*Botanical.*—*Dianthus caryophyllus.*

*Commercial.*—Greenhouse type suitable for cut flower production as a spray.

Parentage:

*Female parent.*—Unnamed seedling (No. 0122).

*Male parent.*—Unnamed seedling (No. 0543).

Plant:

*Height.*—About 41 inches.

*Growing habit.*—Herbaceous, semi-upright.

*Blooming habit.*—Sprays.

*Blooming season.*—Year round.

*Rooting time.*—18–20 days.

*Mutation prone.*—No.

*Disease resistance.*—Unknown.

*Temperature tolerance.*—Typical for carnation.

Foliage:

*Color.*—Upper side: Near to 137A. Lower side: Near to 137A.

*Size.*—About 6½ inches long, about ⅝-inch wide at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem.*—Green.

Bloom:

*Form.*—Circular, high.

*Shape.*—Round.

*Size.*—Diameter average: About 1⅞ to 2⅛ inches.

*Borne.*—Terminal as a spray.

*Color.*—General tonality: Deep pink, near 54B to 54C but may become closer to mauve, near 74C to 73B, depending upon amount of available light.

*Permanence.*—Yes.

*Keeping habit.*—12 to 14 days.

*Fragrance.*—Slight.

*Bloom depth.*—About 1½ inches in August at maturity.

Petals:

*Number.*—About 33.

*Outer petals.*—Length: About 1¼ inches. Width: About 1 inch.

*Texture.*—Smooth.

*Form.*—Fan shaped.

Reproductive organs:

*Styles.*—White.

*Stigmas.*—Lavender pink.

*Filaments.*—White.

*Anthers.*—Light tan.

*Pollen.*—No pollen evident.

I claim:

1. A new and distinct variety of carnation plant, substantially as shown and described, characterized particularly by flowers of attractive mauve coloration.

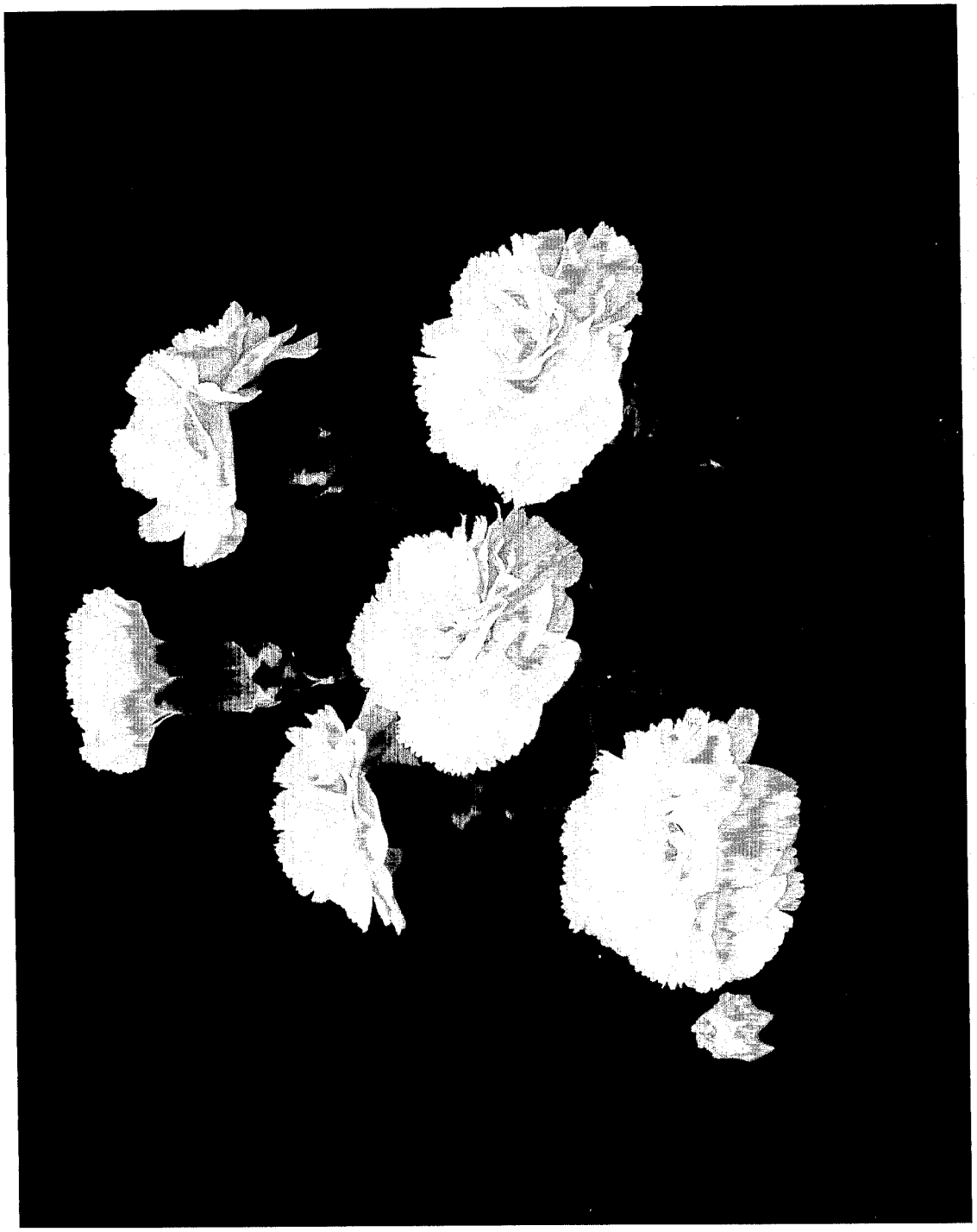

* * * * *